US005639668A

United States Patent [19]
Neel et al.

[11] Patent Number: 5,639,668
[45] Date of Patent: Jun. 17, 1997

[54] OPTICAL APPARATUS FOR PERFORMING AN IMMUNOASSAY

[75] Inventors: Thomas Gary Neel; James E. Lyst, Jr., both of Indianapolis, Ind.

[73] Assignee: Boehringer Mannheim Corporation, Indianapolis, Ind.

[21] Appl. No.: 527,862

[22] Filed: Sep. 14, 1995

[51] Int. Cl.$^6$ .................. G01N 33/552; G01N 33/53
[52] U.S. Cl. .................. 436/172; 385/12; 385/39; 385/42; 385/43; 422/55; 422/82.05; 422/82.08; 422/82.11; 435/287.1; 435/287.2; 435/288.1; 435/288.7; 435/808; 436/164; 436/165; 436/527; 436/805; 436/810
[58] Field of Search .................. 385/12, 39, 42, 385/43; 422/55, 82.05, 82.08, 82.11; 435/287.1, 287.2, 288.1, 288.7, 808; 436/164, 165, 172, 527, 805, 810

[56] References Cited

U.S. PATENT DOCUMENTS

| | | | |
|---|---|---|---|
| 3,998,591 | 12/1976 | Eckfeldt | 23/253 |
| 4,133,639 | 1/1979 | Harte | 23/230 |
| 4,321,057 | 3/1982 | Buckles | 23/230 |
| 4,399,099 | 8/1983 | Buckles | 422/58 |
| 4,447,546 | 5/1984 | Hirschfeld | 436/527 |
| 4,558,014 | 12/1985 | Hirschfeld et al. | 436/527 |
| 4,582,809 | 4/1986 | Block et al. | 436/527 |
| 4,671,938 | 6/1987 | Cook | 422/57 |
| 4,880,752 | 11/1989 | Keck et al. | 435/7 |
| 5,006,716 | 4/1991 | Hall | 250/458.1 |
| 5,093,268 | 3/1992 | Leventis et al. | 436/172 |
| 5,152,962 | 10/1992 | Lackie | 422/681 |
| 5,156,976 | 10/1992 | Slovacek et al. | 436/164 |
| 5,168,156 | 12/1992 | Fischer et al. | 250/227.21 |
| 5,173,434 | 12/1992 | Morris et al. | 436/172 |

OTHER PUBLICATIONS

"Biosensors with Fiberoptics", D. Wise et al., Edistors, Humana Press, Clifton, NJ.

Primary Examiner—Christopher L. Chin
Attorney, Agent, or Firm—Perman & Green, LLP

[57] ABSTRACT

An optical system which may be a component of apparatus for assaying a fluid sample with radiation is capable of exciting fluorescence in fluorescent material and includes a totally internally reflecting, unitary elongated substrate transmissive to both the excitation radiation and to the fluorescence. The fluorescent material includes at least a moiety of an antibody-antigen complex that includes a tag that will provide the fluorescence when excited by an evanescent wave generated by the excitation radiation. The substrate includes an elongated fiber and an integral lens formed to guide the optical radiation into the fiber within the bounds of a critical angle to assure total internal reflectance. A hollow elongated enclosure is disposed concentrically about and spaced from the fiber so as to provide an interspace of capillary dimensions. A test implement supports the elongated substrate such that the fluid sample is caused to flow onto the fiber and, by capillary action, into the interspace between the fiber and the enclosure. The apparatus further includes a source of the excitation radiation, refractive means for focusing the radiation toward the lens substantially in the region thereof at which evanescent wave coupling occurs, detector means for detecting fluorescence radiation emitted from an end of the fiber responsively to the excitation radiation, and optics frame means for mounting all components in fixed relation to the lens for introducing the excitation radiation into the lens within the critical angle.

19 Claims, 5 Drawing Sheets

OPTICAL APPARATUS FOR PERFORMING AN IMMUNOASSAY

BACKGROUND OF THE INVENTION

1. Field of the Invention

This invention relates to immunoassays and to such assays in which a fluorescent tag capable of emitting fluorescent radiation when excited by more energetic exciting radiation is incorporated into a constituent of an antigen-antibody or similar complex. More particularly, this invention relates to optical apparatus used for performing the assay and still more particularly to improved optical apparatus which focuses the excitation radiation onto a substrate coated with the fluorescent material limited substantially to the region at which evanescent wave coupling occurs.

2. Description of the Prior Art

Immunoassay, in which aliquots of sample and one or more reagents are variously reacted to form antigen-antibody or similar complexes which may then be observed in order to assay the sample for the presence and titer of a predetermined moiety of the complex, are well known. Typical of such assays are those wherein a specific antibody is used to measure the quantity of the antigen for which it is specific, or vice versa. However, the technique has been extended to quantitate haptens including hormones, alkaloids, steroids, and the like as well as antigens, and antibody fragments (i.e., Fab) as well as complete antibodies, and it is in this broader sense that the present invention should be understood.

As is well known, sensitive immunoassays employ tracer techniques Wherein a tagged constituent of the complex is incorporated into the reagent, the non-complexed tagged reagent being separated from the complexed reagent, and the complex (or non-complexed reagent) then quantitated by observing the tag. Both radioisotopes and fluorescent markers have been used to tag constituents of immunoassay reagents, the tag being respectively observed by a gamma, ray counter or a fluorometer. The present invention is, however, directed only to those assays which rely on fluorescence.

The separation of the non-complexed tagged moiety from the complexed is commonly accomplished by immobilizing a predetermined one of the components of the complex to a solid phase (such as the inside wall of a test tube, glass or polymeric beads, or the like) in such a way as not to hinder the component's reactivity in forming the complex. As an example, an antibody such as immunoglobulin G (IgG) may be bound by its carboxyl terminations to a solid phase, such as glass, by a silyl compound such as 3-aminopropyltrimethoxysilane, thereby leaving free the antigen reactive amino terminations of the antibody. Any complex formed incorporating the immobilized component may then be physically separated from the non-reacted complement remaining in solution, as by aspirating or decanting the fluid from a tube or eluting the fluid through a particulate bed.

In competition immunoassay, the reagent consists of a known quantity of tagged complement (such as antigen) to the immobilized component of the complex (in this instance, antibody). The reagent is mixed with a fixed quantity of the sample containing the untagged complement to be quantitated. Both tagged and untagged complement attach to the immobilized component of the complex in proportion to their relative concentrations. After incubation for a set time, the fluid sample and reagent are separated. The complex immobilized to the solid phase is then illuminated with radiation of a wavelength chosen to excite fluorescence of the tag, and the fluorescence is measured. The intensity of the fluorescence of the immobilized complex is inversely proportional to the concentration of the untagged complement being assayed.

Alternatively, an assay may be made by immobilizing a quantity of an analog of the moiety to be quantitated (i.e., a substance which is immunologically similarly reactive) and reacting the sample with a known quantity of tagged complement. The tagged complement complexes with both the unknown quantity of the moiety in the sample and the immobilized analog. Again, the intensity of fluorescence of the immobilized complex is inversely proportional to the concentration of the (free) moiety being quantitated.

So-called "sandwich" immunoassays may be performed for multivalent complements to the immobilized component, the attached complement being then further reacted with a tagged analog of the immobilized component. Thus, bivalent antigen may be bound to an immobilized antibody and then reacted with a fluorescent tagged antibody, forming an antibody-antigen-tagged antibody sandwich that may then be separated from the unreacted tagged antibody. The intensity of the fluorescence of the thus formed immobilized complex is directly proportional to the concentration of the species being quantitated.

In any of the assays, accuracy in quantitation is determined in part by the technique of the laboratory personnel performing the assay. Thus, precision fluorescence immunoassay requires fluorometric measurement of a predetermined volume of the sample to which a predetermined quantity of reagent has been added at a known dilution. To insure that the necessary volume measurements are not the accuracy limiting step of the assay requires that the assay be performed by skilled personnel and often with precision apparatus, or alternatively, precisely constructed and pre-loaded disposable reagent kits (to insure the titer of reagent) together with an accurately timed diffusion process (to insure the size of the sample volume assayed.

It will be appreciated that the use of skilled personnel, precision apparatus, and accurate manipulative or timing requirements impact both the cost and wide-scale availability of an assay.

It is well known that optical systems employing the principles of attenuated total internal reflection (ATR) spectroscopy, are useful in chemical and biochemical analysis or assay including immunoarrays. For example, U.S. Pat. No. 4,133,639 discloses a system based on absorption of the evanescent wave by the analyte; U.S. Pat. Nos. 4,321,057 and 4,399,099 both disclose systems that detect changes in the radiation transmitted through the fiber; and U.S. Pat. No. 4,447,546 describes a fluorescence immunoassay system.

In apparatus as described in the aforementioned U.S. Pat. No. 4,447,546, an optical fiber is supported within a capillary tube in approximately concentric alignment therewith. A fluid sample is introduced into the interspace between the fiber and the tube and is drawn into and supported in the interspace by capillary action. To maximize sensitivity and efficiency of such an immunoassay apparatus, it is important that the fiber remain spaced from the internal walls, of the capillary tube. If the fiber contacts the capillary wall, capillary action may be adversely affected. and total internal reflection will not be achieved since radiation will leak out of the fiber at the point of contact between the fiber and the capillary wall with attendant loss of sensitivity.

It is important that the end of the fiber into which optical radiation and from which fluorescent radiation are transmitted be supported in a fixed axial position with respect to an optical system for transmitting optical radiation in and out of the fiber. In the event that end of the fiber does not lie at a fixed position with respect to that optical system, the amount and orientation of transmitted radiation entering the fiber may vary, adversely affecting the accuracy and sensitivity of the apparatus.

Several techniques have been developed in known immunoassay apparatus for properly positioning an optical fiber within a capillary tube. The oldest technique involves supporting the proximal end (i.e. the end into which radiation :s initially launched) of the optical fiber using a conventional Fiber optic connector. Use of these connectors typically involves covering the outer surface of the fiber adjacent its proximal end with a cladding material typically consisting of a transparent high molecular weight polymer. Known cladding materials typically have a refractive index higher than that of the sample, e.g. 1.40 to 1.45, with the result that the numerical aperture of the fiber is reduced to a level at which acceptable sensitivity levels cannot readily be achieved with the apparatus.

Another technique, described in U.S. Pat. No. 4,671,938, involves supporting the fiber in cantilever fashion at its distal end, i.e. the end opposite the end where optical radiation is transmitted into the fiber. The proximal end of an optical fiber supported in this fashion is however displaceable both axially and radially, and such displacement will also cause loss of instrument sensitivity. Further, when the fiber is enclosed in a capillary tube so that a liquid sample being assayed can be introduced into the interspace between the fiber and the capillary tube, the end of the tube surrounding the proximal end of the fiber has not heretofore been readily sealable to prevent leakage of that sample. The toroidal fluid meniscus formed at the end of the tube can serve to prevent fluid flow out of that end of the capillary tube but will, of course, tend to break down when subjected to shock, vibration, high pressure and the like. If the sample being assayed is highly toxic or infectious, such a casual barrier is unacceptable.

In yet another technique for supporting the fiber, the fiber and surrounding capillary tube are disposed in mounting apparatus for attachment to an optical assembly, for transmitting excitation radiation into the proximal end of the fiber and receiving fluorescent radiation emitted from the proximal end of the fiber. Included in the apparatus is a mounting assembly for centering the fiber within the capillary, tube and for biasing the fiber in a first direction against an annular seat. The latter is designed to support one end of the fiber so that none of the radiation introduced into the fiber is intercepted by the seat.

In such total internal reflection systems, the evanescent zone around the fiber increases in depth and the sensitivity of the system also increases as the numerical aperture of the fiber increases. Also the intensity of the fluorescent signal tunnelling back into the fiber is proportional to a very high power of the numerical aperture (as defined in part by the refractive index of the sample in which fluorescence is excited). Thus, it is preferred that the numerical aperture of the system be maximized, particularly by providing the input radiation at as high a flux as possible over a maximum solid acceptance angle. Such maximization has heretofore been limited by the first of the above-described techniques used to clamp and support the fiber, particularly where the diameter of the fiber employed is very small, e.g. 300–400 microns. To obtain very high numerical apertures using a separate mounting assembly, the art has heretofore typically employed highly corrected lenses with shallow depth of field. Such lenses are expensive, and are difficult to manufacture and to maintain in alignment.

SUMMARY OF THE INVENTION

It was in light of the state of the art as just described that the present invention was conceived and has now been reduced to practice.

In one embodiment, an optical system for transforming a solid circular collimated light beam to an annular collimated light beam comprises a first transparent refractive member for intercepting a circular collimated light beam and transforming it into a diverging, coneshaped, annular light beam, and a second transparent refractive member for intercepting the diverging annular light beam from the first refractive member and transforming the cone shaped annular light beam into an annular light beam having substantially constant inner and outer diameters. The first and second refractive members are spaced apart and coaxial with the longitudinal axis of the circular collimated light beam. In another embodiment, an optical transformer includes a solid transparent body having a first refractive surface for redirecting a solid collimated light beam into a diverging light beam having an annular cross section and having a second refractive surface for redirecting the diverging light beam into a light beam having an annular cross section of substantially constant diameter.

In either embodiment, this optical system may be a component of apparatus for assaying a fluid sample with radiation which is capable of exciting fluorescence in fluorescent material and including a totally internally reflecting, unitary elongated substrate transmissive to both the excitation radiation and to the fluorescence. In such an instance, the fluorescent material includes at least a moiety of an antibody-antigen complex that includes a tag that will provide the fluorescence when excited by an evanescent wave generated by the excitation radiation. The substrate includes an elongated fiber and an integral lens formed to guide the optical radiation into the fiber within the bounds of a critical angle to assure total internal reflectance. A hollow elongated enclosure is disposed concentrically about and spaced from the fiber so as to provide an interspace of capillary dimensions. A test implement supports the elongated substrate such that the fluid sample is caused to flow onto the fiber and, by capillary action, into the interspace between the fiber and the enclosure. The apparatus further includes a source of the excitation radiation, refractive means for focusing the radiation toward the lens substantially in the region thereof at which evanescent wave coupling occurs, detector means for detecting fluorescence radiation emitted from an end of the fiber responsively to the excitation radiation, and optics frame means for mounting all components in fixed relation to the lens for introducing the excitation radiation into the lens within the critical angle.

A principal object of the present invention is therefore to provide an improved fiber-optic assay system that improves the performance and outcome of an immunoassay.

Another object of the present invention is to provide such an assay system in which the energy of the light source is used most efficiently.

Still another object of the invention is to provide a system for assaying a fluid sample with excitation radiation from a radiation source, which radiation is capable of exciting fluorescence in fluorescent material, and including a totally internally reflecting, unitary elongated fiber transmissive to both the excitation radiation and to the fluorescence, the fiber having an end into which the radiation is to be introduced and a peripheral surface, at least a portion of which, is adapted to contact the sample and a source of the excitation radiation and an optical mechanism for guiding the excitation radiation into the fiber within the bounds of a critical angle to assure total internal reflectance and for focusing the excitation radiation onto the substrate limited substantially to the region thereof at which evanescent wave coupling occurs.

Still a further object of the invention is to provide such an assaying system wherein the source of the excitation radiation provides a solid collimated beam of light, wherein the optical means includes an optical transformer for redirecting the solid collimated beam into a beam having an annular cross section of substantially constant cross section and a converging lens between the optical transformer and the introduction end of the fiber for focusing the annular cross section beam from the optical transformer into the fiber.

Still another object of the invention is to provide such an assaying system wherein the optical transformer includes a first transparent refractive member having a first leading surface positioned to intercept the circular collimated light beam for transforming the circular collimated light beam into a diverging annular light beam and a base surface lying in a plane perpendicular to the axis of the collimated light beam and a second transparent refractive member having a second leading surface positioned to intercept the diverging annular light beam from the first refractive member for transforming the cone shaped annular light beam into an annular light beam having a substantially constant inner and outer diameters, the first and second refractive members being spaced apart and coaxial with the longitudinal axis of the circular collimated light beam.

Yet a further object of the invention is to provide such an assaying system wherein the first refractive member has a leading surface which is a circular cone facing the collimated light beam and wherein the second refractive member has a leading surface which is a circular cone facing the diverging annular light beam.

Still a further object of the invention is to provide such an assaying system wherein the elongated fiber is cylindrical and adapted to receive a coating of the fluorescent material on at least a portion of its peripheral surface.

Yet another object of the invention is to provide such an assaying system wherein the elongated fiber is cylindrical and adapted to receive on at least a portion of the peripheral surface a coating of the fluorescent material thereof which includes at least a moiety of an antibody-antigen complex that includes a tag that will provide the fluorescence when excited by an evanescent wave generated by the excitation radiation.

A further object of the invention is to provide such an assaying system wherein a hollow elongated enclosure is disposed about and spaced from the fiber so as to provide an interspace between the fiber and the enclosure.

Still a further object of the invention is to provide such an assaying system wherein the elongated fiber is cylindrical, is disposed concentrically within the enclosure, and wherein the interspace between the enclosure and the fiber is of capillary dimensions.

Yet a further object of the invention is to provide an optical system for transforming a solid circular collimated light beam to an annular collimated light beam comprising a first transparent refractive member having a first leading surface positioned to intercept the circular collimated light beam for transforming the circular collimated light beam into a diverging annular light beam and a base surface lying in a plane perpendicular to the axis of the collimated light beam and a second transparent refractive member having a second leading surface positioned to intercept the diverging annular light beam from the first refractive member for transforming the cone shaped annular light beam into an annular light beam having a substantially constant diameter, the second refractive member having a base lying in a plane perpendicular to the axis of the collimated light beam, the first and second refractive members being spaced apart and coaxial with the longitudinal axis of the circular collimated light beam.

Still another object of the invention is to provide such an optical system wherein the first refractive member has a leading surface facing the collimated light beam which is a circular cone and wherein the second refractive member has a leading surface which is a circular cone facing the diverging annular light beam.

A further object of the invention is to provide an optical transformer including a solid transparent body having a first refractive surface for redirecting a solid collimated light beam into a diverging light beam having an annular cross section and having a second refractive surface for redirecting the diverging light beam into a light beam having an annular cross section of substantially constant diameter.

Another object of the invention is to provide such an optical system wherein the optical transformer includes a first refractive element having a first conical surface onto which the solid collimated light beam is directed for redirecting the light beam into the diverging annular light beam and a second refractive element having a second conical surface for receiving the diverging annular light beam from the first lens element and for redirecting the diverging annular light beam into a beam having an annular cross section of substantially constant cross section.

Yet another object of the invention is to provide such an optical system wherein the first and second refractive elements are spaced apart and coaxial with the longitudinal axis of the circular collimated light beam.

Still another object of the invention is to provide such an optical system wherein the first refractive element has a leading surface facing the collimated light beam which is a circular cone and wherein the second refractive element has a leading surface facing the diverging annular light beam which is a circular cone.

Other and further features, advantages, and benefits of the invention will become apparent in the following description taken in conjunction with the following drawings. It is to be understood that the foregoing general description and the following detailed description are exemplary and explanatory but are not to be restrictive of the invention. The accompanying drawings which are incorporated in and constitute a part of this invention, illustrate one of the embodiments of the invention, and, together with the description, serve to explain the principles of the invention in general terms. Like numerals refer to like parts throughout the disclosure.

DETAILED DESCRIPTION OF THE PREFERRED EMBODIMENTS

The present invention is applicable to an immunoassay system which operates by total reflection fluorescence, coupled with tunneling of the fluorescent radiation.

Figure 1:
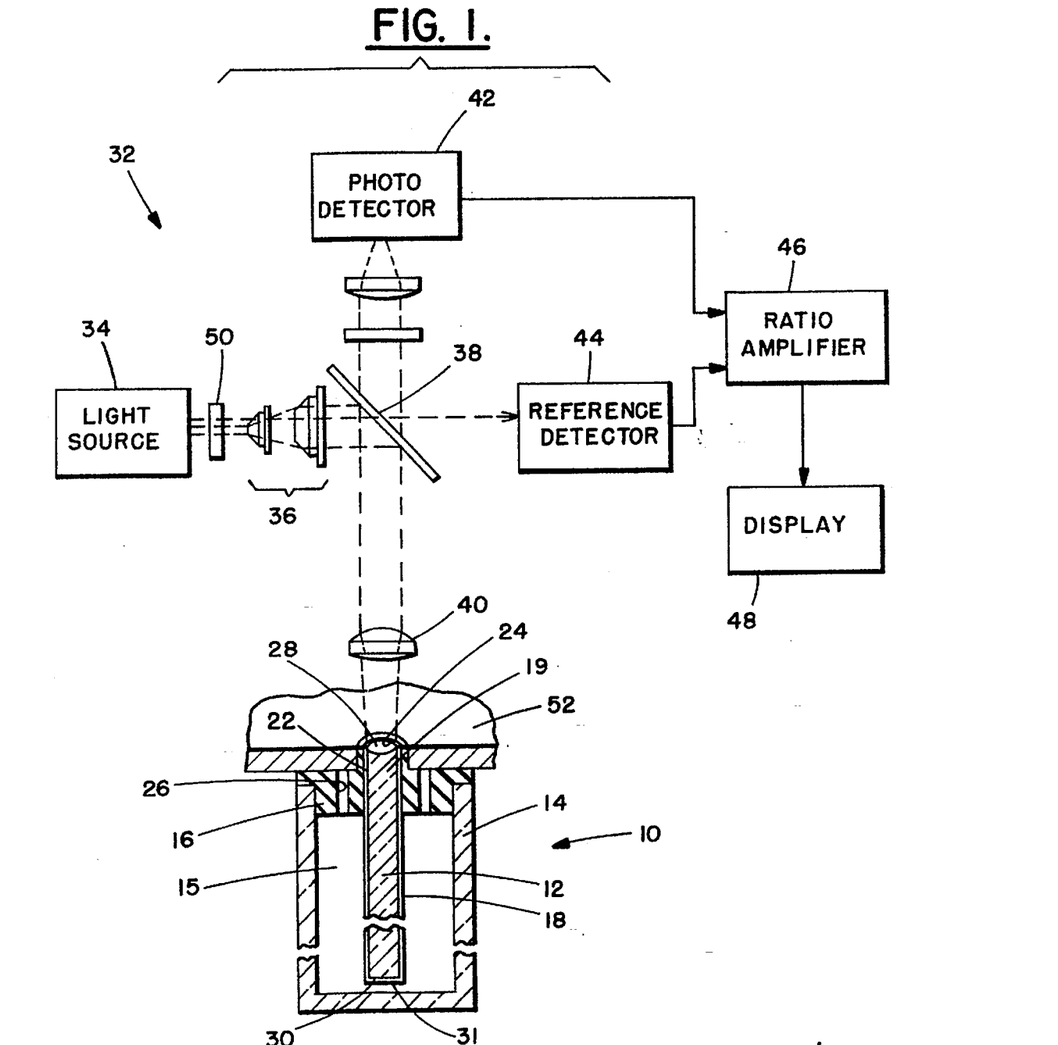
FIG. 1 is a diagrammatic illustration, certain parts being shown in cross section for clarity, depicting an immunoassay system embodying the present invention.

Referring to FIG. 1, there may be seen a longitudinal cross sectional view of an immunoassay kit 10 which comprises an optical fiber 12, a capillary tube 14 filled with a fluid sample 15 to be assayed, and a stopper 16.

Fiber 12 is an elongate substantially cylindrical optically transparent body adapted to propagate along its length through multiple total internal reflections optical radiation entering an end of the fiber within an established solid angle substantially rotationally symmetric about the axis of the fiber. As is well known in the art of fiber optics, the maximum acceptance angle B, with regard to the fiber axis for the radiation entering the fiber and so propagated within it, is established by the refractive indices of the fiber and the surrounding medium. For radiation initially propagating through a medium of refractive index $n_o$ incident upon a fiber of refractive index $n_1$ otherwise surrounded by a material of refractive index $n_2$, the maximum acceptance angle may be found from the equation $$N.A.=n_o\sin B=(n_1^2-n_2^2)^{1/2} \quad (1)$$

where:

N.A. is the so-called numerical aperture of the fiber;

B is the maximum acceptance angle for radiation entering the fiber 12;

n is the optical index of the fiber;

$n_2$ is the optical index of the sample; and $n_o$ is the optical index of the ambient medium.

By way of example, but not limitation, fiber 12 may be any of a number of optically transparent materials, such as glass, quartz, polypropylene, polyolefin, nylon, or the like, chosen to have an index of refraction greater than that of the fluid sample being assayed (typically, an aqueous solution having an index of refraction near 1.33 or a serum sample having an index of refraction near 1.35) and further chosen to be relatively insoluble and non-reactive with the fluid. While other fiber diameters may be used, it has been found that 200 microns is satisfactory. For most assays, a fiber 25 mm in length appears adequate; however, it will be understood that the length of the fiber can be accommodated to the assay to be undertaken.

Fiber 12 is provided with a surface coating 18 including means for attaching selected moieties of an antigen-antibody complex. As herein used, "antigen-antibody complex" includes complexes not only of complete antibodies and antigens, but complexes incorporating the immunologically reactive fragments of either or both.

Capillary tube 14 is preferably an optically transparent tube, its material of construction also being chosen to be relatively insoluble and non-reactive with the fluid being assayed. Thus, capillary tube 14 is preferably fabricated from such materials as glass, quartz, polypropylene, polyolefin, or the like. In a preferred embodiment, the capillary tube 14 is of right circular cylindrical bore, having an inside diameter a few hundred microns larger than the diameter of the fiber 12 (e.g., for a fiber diameter of 200 microns, the capillary tube 14 may have an inside diameter of about 800 microns).

Stopper 16 is configured and dimensioned to fit within an end of the capillary tube 14 and support an end portion 19 of fiber 12 substantially coaxially within the capillary tube. To this end, stopper 16 is preferably provided with a flange 20 having an overall diameter on the order of the outside diameter of capillary tube 14 and a centrally disposed ferrule-like extension 22 coaxial with a central bore 24. Bore 24 penetrates throughout stopper 16, and is dimensioned to secure the end portion of fiber 12. The stopper 16 may actually be molded in place about fiber 12, the stopper being preferably fabricated of a low index material, such as siloxane. Stopper 16 may be further provided with one or more through perforations 26 communicating with the interior of capillary tube 14.

Fiber 12 passes through and is supported by stopper 16 so as to expose substantially all of the fiber except for its end portion to the interior of capillary tube 14, leaving an end face 28 unobscured and coterminous with the extremity of bore 24 external to the capillary tube. End face 28 is preferably planar and disposed normal to the axis of fiber 12. Preferably, end face 28 is also highly transparent and free of blemishes which would tend to scatter light incident upon the end face 28. To this end, end face 24 may be optically polished, although it has been found that a fused quartz fiber may be cleaved to provide an adequate optical surface. Optionally, an end face 30 of the fiber 12 distal from end face 28 may also be polished flat or cleaved and further provided with a mirror coating 31 (or a separate mirror) disposed substantially normal to the fiber axis, thereby causing radiation trapped in the fiber to double pass the fiber. The overall dimensions of fiber 12, capillary tube 14, and stopper 16 are chosen to insure that the lower end face of the fiber is also within the capillary tube.

Prior to being assembled into kit 10, fiber 12 is provided the coating 18 activating a region of its cylindrical surface for the assay to be performed. The activated region may be restricted to a predetermined length of fiber 12 in any suitable fashion. The dimensions of the activated region may be controlled, for example, by masking the fiber during coating or, alternatively, the entire length of fiber 12 might be activated and the length of the fiber disposed within capillary tube 14 carefully controlled.

For a detailed description of the assay operation performed by and within the kit 10, the reader's attention is directed to the disclosure of U.S. Pat. No. 4,447,546 to Hirshfeld which is incorporated herein in its entirety, by reference.

Kit 10 is intended for use with an immunoassay system 32 which comprises a light source 34, a dichroic beam splitter 38, an objective lens 40, a photodetector 42, a reference detector 44, a ratio amplifier 46, and a display 48.

The light source 34 provides optical radiation of the appropriate frequency, chosen on the basis of the fluorophor used as the tag in the assay of interest, to excite fluorescence in the tagged component of the reagent. Light source 34 preferably provides this radiation over only a narrow wavelength band, chosen to maximize the fluorescence. Hence, light source 34 typically includes, in addition to the preferred tungsten-halogen lamp and associated power supply, a band-pass or excitation filter 50. Alternatively, it will be understood that light source 34 might incorporate other sources, such as a mercury lamp, flash lamp, or a laser. In this regard, it is noteworthy, but not critical to the present invention, that a solid state light source is preferable to a white light source. This is for the reason that it generates less heat, its unit size is smaller, has greater optical output, is monochromatic such that only desired wavelengths are provided, and is directional with resulting ease of control of the light beam. The optical transformer, which will be described at greater length below, constitutes an appropriate beam shaping aperture and optics, as will be understood by those skilled in the art, to illuminate objective lens 40 with a beam of the appropriate vergence so as to permit the objective lens to image the source aperture on end face 28 of fiber 12 with no ray incident on the end face at an angle of incidence greater than that corresponding to the numerical aperture of the fiber.

Interposed between the light source 34 and the objective lens 40 is the dichroic beamsplitter 38. In the preferred embodiment, beamsplitter 38 is a low-pass interference filter with a cut-off frequency chosen to be between the frequencies of maximum absorption and maximum fluorescence emission of the fluorophore of interest. Beamsplitter 38 thus reflects the high frequency (short wavelength) fluorescence exciting radiation from light source 34 and transmits the low frequency radiation corresponding to the fluorescence maximum of the fluorophor.

Objective lens 40 is selected to image light source 34 on the end face 28 of the fiber 12, so as to just fill the end face with an image of the beam shaping aperture of the source, the maximum angle of incidence of a ray being selected to be less than that corresponding to the numerical aperture of the fiber. The objective lens 40 is also selected so as to collect substantially all of the radiation exiting end face 28 over the numerical aperture of the fiber and image the end face at the photodetector 42. As an aid in establishing the proper position of fiber 12, immunoassay system 32 is preferably provided with a positioning means, such as aperture plate 52, dimensioned to accept ferrule-like extension 22 of stopper 16 and disposed to position end face 24 appropriately relative to the objective lens 40.

The photodetector 42 is positioned to receive, through beamsplitter 38, an image of end face 28 of fiber 12 projected toward the photodetector by the objective lens 40. The photodetector 42 preferably includes a photomultiplier (provided with an appropriate power supply and field optics to restrict the detector's field of view to end face 28, as is well known in the art), chosen to have maximum sensitivity in the region of peak fluorescence of the fluorophor. The photodetector 42 is further preferably provided with a blocking filter corresponding to the band-pass filter 50 provided with light source 34.

Reference detector 44, preferably a photodiode, is disposed to intercept radiation from light source 34 passing through dichroic beamsplitter 38. Reference detector 44 is chosen for peak sensitivity in the spectral region of light source 34 passed by dichroic beamsplitter 38, and includes appropriate field stops and optics to limit its field of view to the source.

Ratio amplifier 46 is any of a number of well-known electronic devices providing an output signal which is proportional to the ratio of a pair of input signals, so connected to the outputs of photodetector 42 and reference detector 44 as to provide a signal proportional to the ratio of the output of the photodetector to the reference detector. For instance, ratio amplifier 46 may be a variable gain amplifier amplifying the output from photodetector 42 and having a gain inversely proportional to the output from reference detector 44.

The output of ratio amplifier 46 is connected to and serves as the input for display 48. Display 48 may be any of a number of devices that provides a visual signal proportional to an electrical input, and may be, for instance, a meter, a digital display, a strip chart recorder, or the like.

In operation, the kit 10 is dipped into a sample to be assayed. Perforations 23 allow capillary tube 14 to fill itself by capillary action once its end is immersed in sample. A fixed volume of sample will thus be drawn into capillary tube 14 whenever it is dipped in the solution and allowed to fill sufficiently to cover the active region of the fiber 12.

After incubation, the kit 10 is placed into the system 32, the stopper 16 cooperating with the aperture plate 52 to position the end face 28 of the fiber 12 in the appropriate location relative to the optical train of the system 32. Radiation of a wavelength chosen to excite fluorescence in fluorophores within the sample 15 is supplied by the light source 34, via dichroic beam splitter 38 and the objective lens 40, so as to illuminate the end face 28 of the fiber 12 within the cone angle defined by the numerical aperture of the fiber. This radiation is consequently propagated within fiber 12 at or above the critical angle so as to be totally internally reflecting along the length of the fiber. As a result, an evanescent wave is produced in the fluid sample 15 adjacent the fiber. For a detailed discussion of the diagnostic characteristics of the assay performed, reference is again made to Pat. No. 4,447,546.

The optical transformer 36 by means of which the beam of light 34 is converted from a circular collimated light beam to an annular collimated light beam having clearly defined inner and outer dimensions will now be described. The goal sought, and achieved, by the invention is to maximize the output or signal provided by the light source 34 or, conversely, to minimize its required intensity while enabling performance of the assay.

Figure 2:
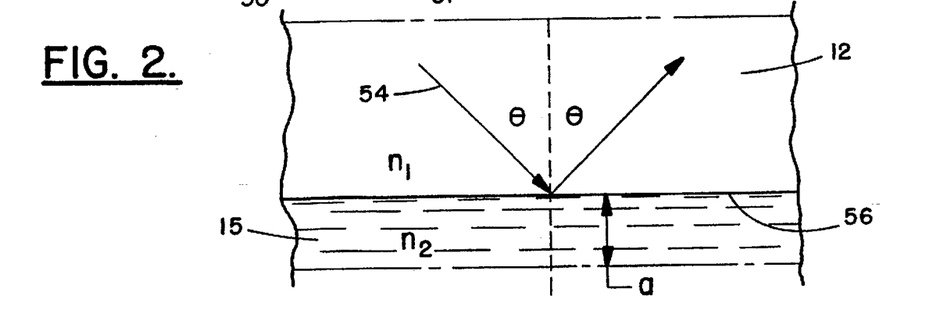
FIG. 2 is a detail cross section view of a portion of the optical fiber illustrated in FIG. 1 and depicting the reflection of a light ray at the interface of the fiber and of a sample received thereon to be assayed.

FIG. 2 depicts the reflection of a light ray 54 at the glass- (or plastic)-sample interface for the fiber 12. For purposes of the invention, the incident angle $\Theta$ of the incoming and of the reflected light ray 54 must be equal to, or greater than, the critical angle. That is, the light ray 54 does not penetrate the peripheral wall 56 of the fiber but continues being deflected by the peripheral wall as it travels, until it reaches the mirror coating 31 at the end face 30 and returns toward the end face 28. The dimension $\underline{a}$ represents the depth of penetration of the evanescent wave resulting from the travel of the light ray 54 through the fiber 12.

Figure 3:
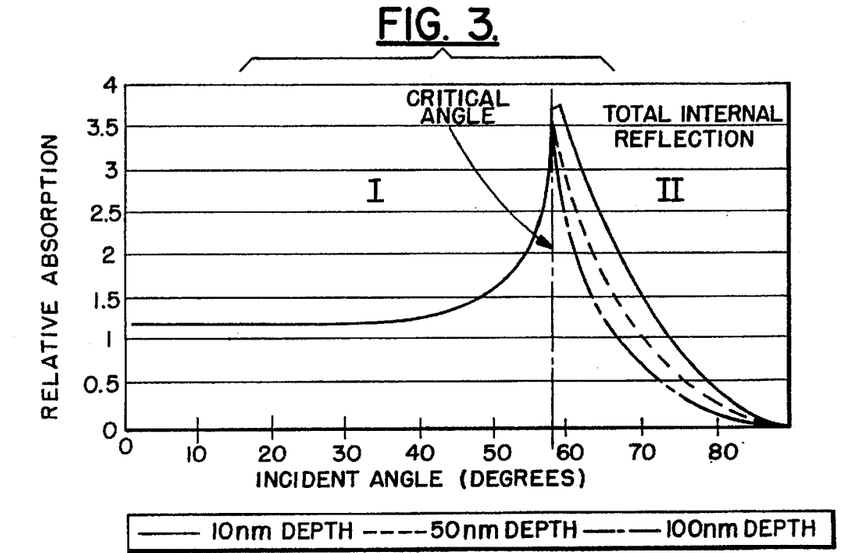
FIG. 3 is a graph depicting the relative absorption of input light into the optical fiber for an entire range of incident angles, $\Theta$.

FIG. 3 is a graph of the relative absorption of input light at a distance $\underline{a}$ away from the peripheral wall 56, that is, from the interface between the fiber 12 and the sample 15. For values of $\Theta$ less than the critical angle, absorption I is defined by the following equation:

$$I = u(k)^2 \cdot 4[1 + \sqrt{(1 - n^2\sin^2\theta)} / n\cos\theta] \quad (2)$$

For values of $\Theta$ greater than the critical angle, absorption I is defined by the following equation:

$$I = u(k)^2 \cdot 4 [n^2\cos^2\theta / (n^2 - 1)]^{[-2ak\sqrt{n^2\sin^2\theta - 1})]} \quad (3)$$

where, in each instance:

$n = n_1/n_2$ = a simple ratio used in equations (2) and (3) where $n_1$ = optical index of refraction of the fiber 12 and $n_2$ = optical index of refraction of the sample 15;

k and K are wave vectors; and u is a complex amplitude as a function of k.

Given a, $n_1$ and $n_2$, a similar graph could be constructed explaining the e-wave absorption as a function of $\Theta$. In any event, the relative graph depicted in FIG. 3 displays the importance of inputting light near the critical angle since absorption is highest in this region. Simply put, higher absorption means higher fluorescence.

Figure 4:
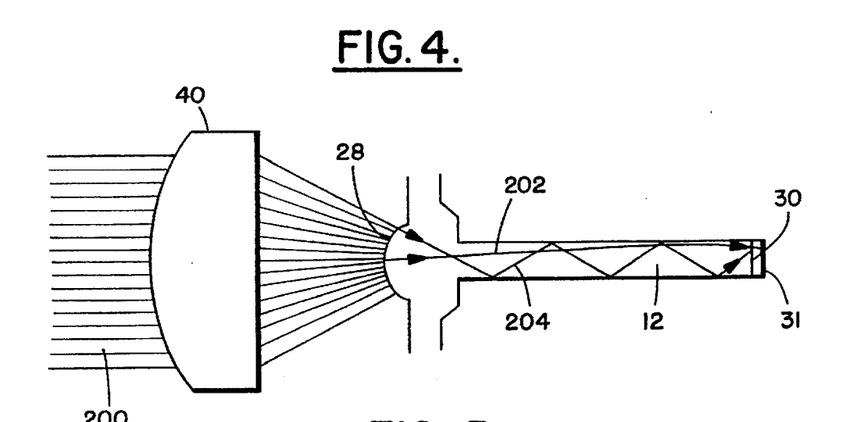
FIG. 4 is a detail cross section view of the optical fiber and of the objective lens as illustrated in FIG. 1 and depicting the internal reflection of light rays within the fiber when conventional light radiation is used.

This concept can be more clearly seen in FIG. 4 which illustrates the effect of a conventional solid collimated light beam 200 when introduced via the objective lens 40 into the optical fiber 12. The central regions of the light beam 200 as exemplified by a light ray 202 strike the side wall of the fiber 12 at a shallow incident angle which achieves only minimal absorption. However, peripheral regions of the light beam 200 as exemplified by a light ray 204 strike the side wall of the fiber 12 at an incident angle which is approximately equal to the optimum angle depicted in the graph of FIG. 3. Unfortunately, most of the light energy in the beam 200 is ineffectual for purposes of the immunoassay and even adds to noise due to scatter and imperfections in the optical path.

Figure 5:
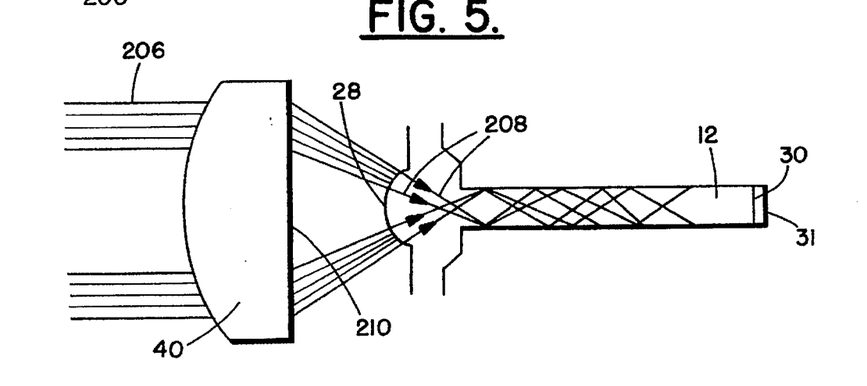
FIG. 5 is a detail cross section view of the optical fiber and of the objective lens, similar to FIG. 4, but depicting the internal reflection of light rays within the fiber when light radiation is used as modified by the optical transformer of the invention.

In contrast, turn to FIG. 5 which illustrates an annular collimated light beam 206 when introduced via the objective lens 40 into the optical fiber 12. In this instance, light rays 208 from the concentrated collimated light beam 206 all strike the side wall of the fiber 12 at a range of incident angles which is approximately equal to the optimum angle depicted in the graph of FIG. 3 but in no case less than the critical angle. Hence, the effectiveness of the energy from the light source 34 is optimized. A blocking disk (not shown) could be applied to the central regions of an aft surface 210 of the objective lens 40 to achieve a similar trace to that of the light rays 208, but such an expedient would waste light energy and would significantly block the return signal from the distal end face of the fiber. With the invention, no light enters the fiber at a shallow angle and all light serves a useful purpose.

Figure 6A:
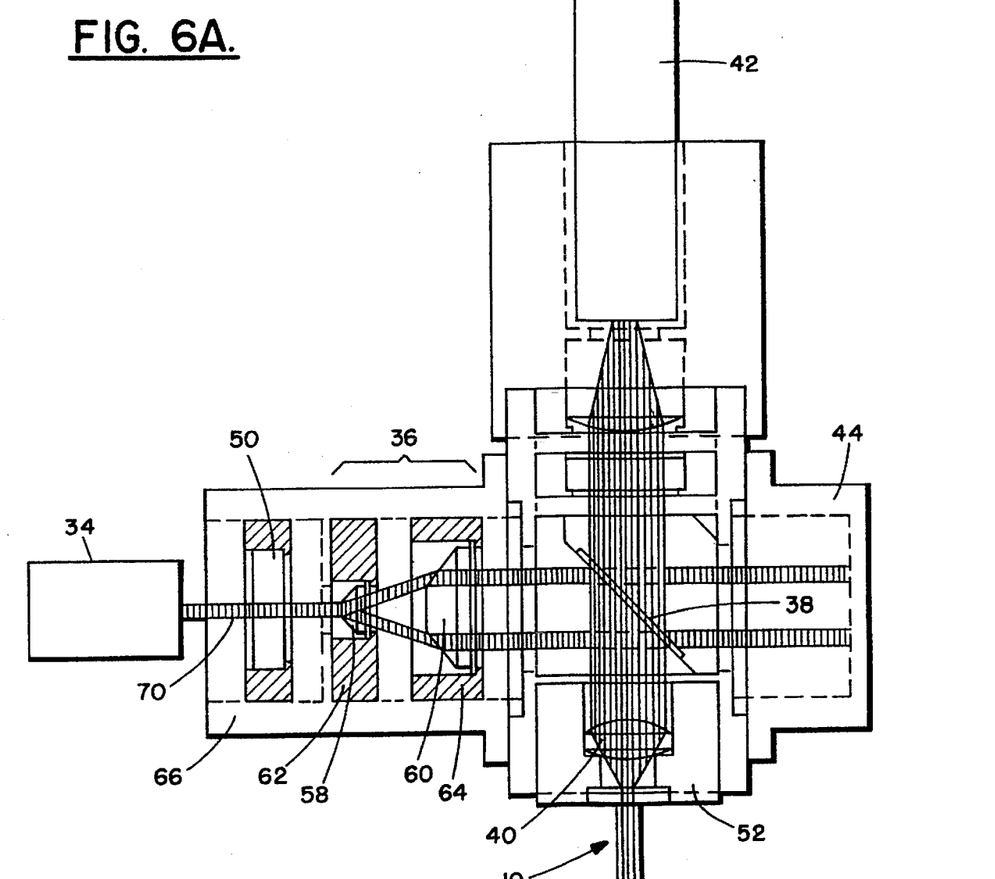
FIG. 6A is a diagrammatic view, illustrating in greater detail, certain components illustrated FIG. 1.
Figure 6B:
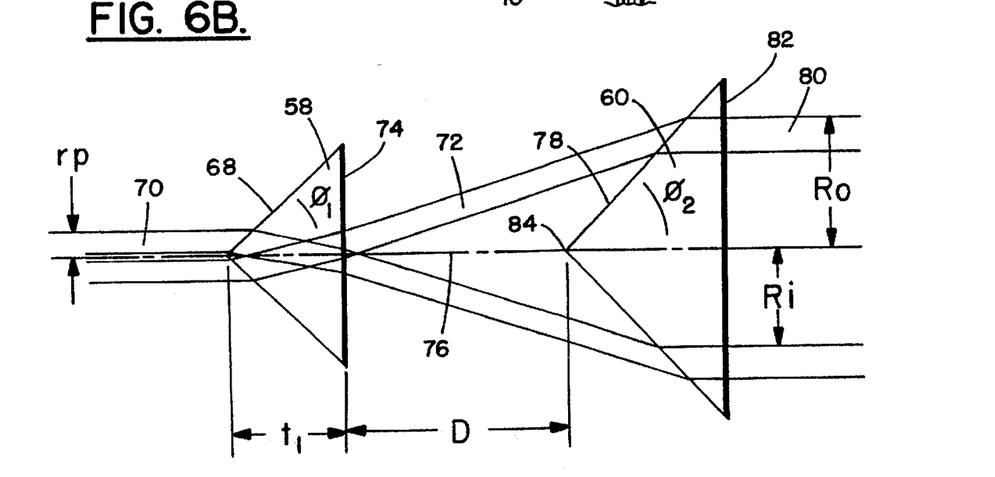
FIG. 6B is diagrammatic side elevation view of one embodiment of an optical transformer according to the invention, as illustrated in FIG. 6A.

It was with a realization of the foregoing principles that the optical transformer 36 was devised. In one embodiment as illustrated in FIGS. 6A and 6B, first and second spaced refractive members 58, 60 are suitably supported in respective holders 62, 64, respectively, on a housing 66 intermediate the filter 50 and the beam splitter 38. The refractive members 58, 60 are transparent, being of optical glass or plastic which is substantially free of contaminants and defects. The refractive member 58 has a first leading surface 68 positioned to intercept the circular collimated light beam 70 having a radius $r_p$ from the light source 34 and serves to transform the light beam into a diverging, or cone-shaped, annular light beam 72. The diverging annular light beam 72 exits the refractive member 58 through a base surface 74 which, if planar, is perpendicular to the axis 76 of the collimated light beam 70.

The second refractive member 60 is spaced from the refractive member 58 and has a second leading surface 78 positioned to intercept the diverging annular light beam 72 as it travels from the refractive member 58. The refractive members 58, 60 are also coaxial with the longitudinal axis 76 of the circular collimated light beam 70. The leading surface 78 serves to transform the annular light beam 72 into an annular, or doughnut-shaped, light beam 80 having substantially constant inner and outer radii, $R_i$ and $R_o$, respectively. The second refractive member 60, as in the instance of the refractive member 58, has a base surface 82 which, if planar, lies in a plane perpendicular to the axis 76 of the collimated light beam 70 and the further modified constant diameter annular light beam 80 exits the refractive member 60 through the base surface 82. While the surfaces 74 and 82 are not necessarily planar, non-planar constructions substantially add to the complexity of the design of the optics for the optical transformer 36. However, it may be desirable to have non-planar constructions in order to increase the optical throughput of the optical transformer.

Using trigonometry with Snell's law $$n_1 \sin\Theta_1 = n_0 \sin\Theta_0 \quad (4)$$

where:

$n_o$ = optical index of refraction of a refractive member;

$n_1$ = optical index of refraction of the surrounding medium;

$\Theta_o$ = an initial angle between the light ray and the normal of the interface between the refractive member and the surrounding medium; and $\Theta_1$ = a resultant angle from the light ray and the normal of the interface between the refractive member and the surrounding medium.

equations for the optics of the invention can be solved. Snell's law describes the bending of light at each interface, that is, between the surrounding medium and each refractive member. The apex angle $\Phi_1$ subtending the leading surface 68 of the first refractive member 58 may be any desired angle although for ease of fabrication, it may be desirable for it to be 45° such that the leading surface 68 in fact defines a right circular cone.

The operation resulting in the design of the optical transformer 36 of FIGS. 4A and 4B will now be described. After arbitrarily choosing the apex angle $\Phi_1$ and the index of refraction for the refractive members 58, 60, the apex angle $\Phi_2$ for the refractive member can be calculated, as follows:

$$\Phi_2 = \tan^{-1}((n - \cos(\sin^{-1}k))/k) \quad (5)$$

where, $$k = n(\sqrt{(1 - \cos^2\Phi_1/n^2)} \cos\Phi_1 - \sin\Phi_1\cos\Phi_1/n)$$

Knowing the apex angles, $\Phi_1$ and $\Phi_2$, the thickness, or height, $t_1$ of the refractive member 58, and the desired outer radius $R_0$ of the constant diameter annular light beam 80, or "ring of fire", the distance D between the refractive members 58, 60 can be calculated. Specifically, the distance D is measured along the axis 76 between the base surface 74 and the apex 84 of the refractive member 60. The calculation is as follows:

$$D = (R_o - r_o)/\tan\theta' - x \tag{6}$$

where $\theta = \sin^{-1}(\cos\Phi_1/n)$;

$\theta' = \sin^{-1}(n\cos(\Phi_1 + \theta))$;

$r_o = t_1(\cot(\Phi_1 + \theta))$; and $x = R_o/\tan\Phi_2$.

Knowing the apex angles, $\Phi_1$ and $\Phi_2$, an intermediate angle, $\Theta'$ (above), and the desired inner radius $R_1$ of the "ring of fire" 80, the radius $r_p$ of the input collimated light beam 70 can be calculated, as follows:

$$r_o = (R_o - R_1)\sin(\Phi_2 - \theta)\sin\Phi_1/(\sin\Phi_2\cos\theta'). \tag{7}$$

Figure 7:
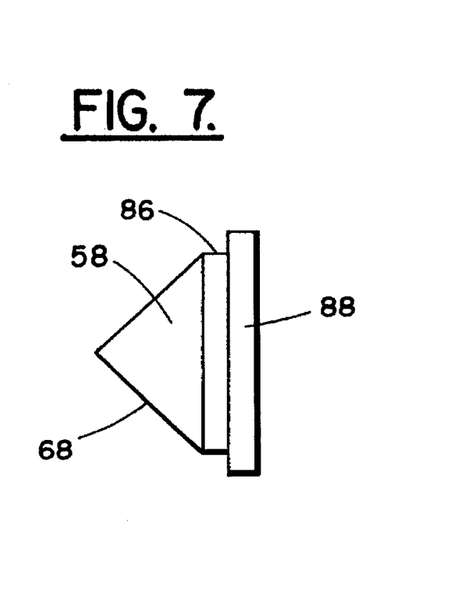
FIG. 7 is a side elevation view illustrating one component of the optical transformer of FIG. 6B, being exemplary of a commercial design.
Figure 8:
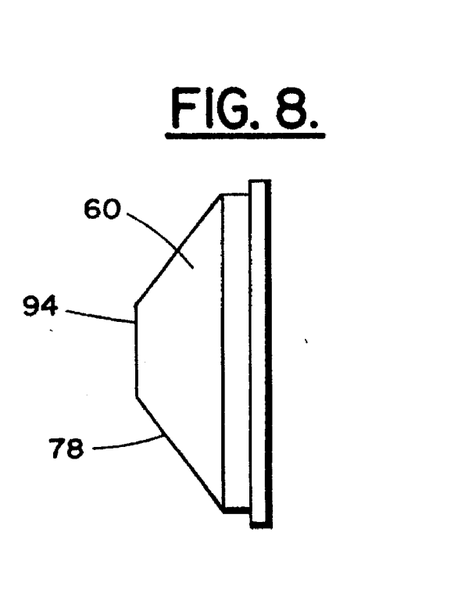
FIG. 8 is a side elevation view illustrating another component of the optical transformer of FIG. 6B, being exemplary of a commercial design.

While the shapes of the refractive members 58, 60 presented in FIG. 6B for the purpose of explaining the design considerations involved in constructing the optical transformer 36 are acceptable for that purpose, in actual fact, they may appear as illustrated in FIGS. 7 and 8, respectively. As to the refractive member 58, for example, the conical first leading surface 68 may lead into a cylindrical surface 86 and thence into a cylindrical flange 88 desirable as a mount for support in the holder 62 of the housing 66. As to the refractive member 60, for example, the conical second leading surface 78 may lead into a cylindrical surface 90 and thence into a cylindrical flange 92 desirable as a mount for support in the holder 64 of the housing 66. In this latter instance, it may be desirable to eliminate the apex 84 to provide a truncated forward facing surface 94 lying in a plane perpendicular to the axis 76. The surface 94 may be provided with a suitable opaque coating to thereby operate as a blocking disk to block stray unwanted light which would otherwise result in lower system resolution. It is noteworthy that use of the surface 94 in this manner will not block desired fluorescence from the fiber 12.

Figure 9A:
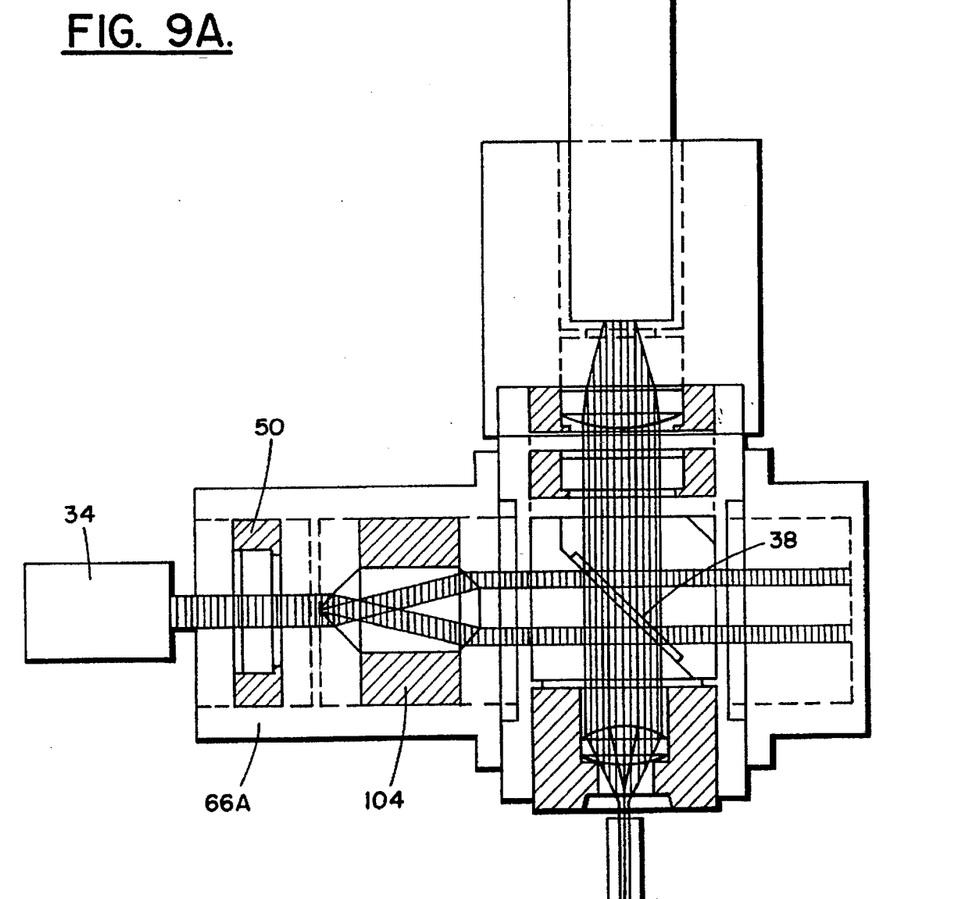
FIG. 9A is a diagrammatic view, illustrating in greater detail, another embodiment of certain components illustrated FIG. 1.
Figure 9B:
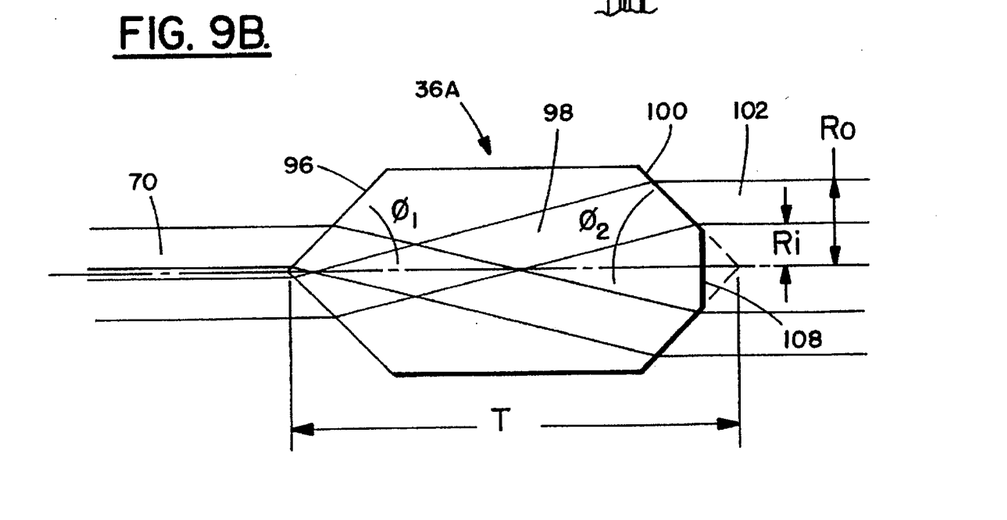
FIG. 9B is diagrammatic side elevation view of another embodiment of an optical transformer according to the invention, as illustrated in FIG. 9A.

In another embodiment as illustrated in FIGS. 9A and 9B, an optical transformer 36A includes a solid transparent cylindrical body of optical glass or plastic which is substantially free of contaminants and defects. The modified optical transformer 36A has a first conical refractive surface 96 subtending an apex angle $\Phi_1$ for redirecting the solid collimated light beam 70 into a diverging, or conical, light beam 98. The optical transformer 36A also has a second, opposite facing, conical refractive surface 100 for redirecting the diverging light beam 98 into an exiting light beam 102 which is doughnut-shaped, having an annular cross section of substantially constant nominal diameter and constant cross section and having substantially constant inner and outer radii, $R_1$ and $R_o$, respectively. The modified optical transformer 36A is supported in a suitable holder 104 on a housing 66A intermediate the filter 50 and the beam splitter 38.

As in the instance of the optical transformer 36, the apex angle $\Phi_1$ subtending the leading surface 96 of the modified optical transformer 36A may have any desired angle although for ease of fabrication, it may be desirable for it to be 45° such that the leading surface 96 in fact defines a right circular cone.

The operation resulting in the design of the modified optical transformer of FIGS. 9A and 9B will now be described. After arbitrarily choosing the apex angle $\Phi_1$, the index of refraction, and the desired outer radius $R_o$ of the resulting annular light beam 102, or "ring of fire", the apex to apex (imaginary) thickness T of the device can be calculated, as follows:

$$T = R_o(\cot\Phi_1 + \tan(\Phi_1 + \sin^{-1}(90 - \theta_1)/n))) \tag{8}$$

The input beam radius $r_p$ can then be calculated, using the desired outer and inner radii, $R_o$ and $R_1$, respectively of the "ring of fire", as follows:

$$r_p = R_o - R_1 \tag{9}$$

Figure 10:
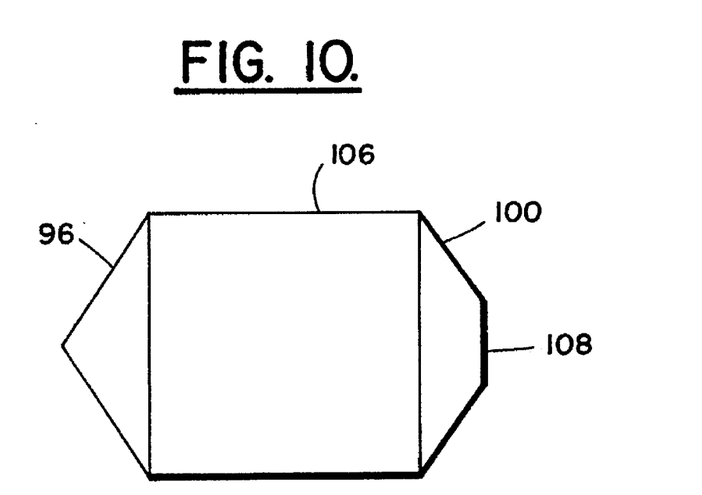
FIG. 10 is a side elevation view illustrating the optical transformer of FIG. 9B, being exemplary of a commercial design.

While the shape of the modified optical transformer 36A presented in FIG. 9B for the purpose of explaining the design considerations involved in its construction are acceptable for that purpose, in actual fact, it may appear as illustrated in FIG. 10. The right conical first refractive surface 96 may lead into a cylindrical surface 86 for support in the holder 104 of the housing 66A. The conical trailing or second refractive surface 100 may lead into a truncated rearward facing surface 108 lying in a plane perpendicular to the axis 76. As in the instance of the truncated surface 94 of the optical transformer 36, the surface 108 may be provided with a suitable opaque coating to thereby operate as a blocking disk to block stray unwanted light which would otherwise result in lower system resolution. Again, it is noteworthy that use of the surface 108 in this manner will not block desired fluorescence from the fiber 12.

While preferred embodiments of the invention have been disclosed in detail, it should be understood by those skilled in the art that various other modifications may be made to the illustrated embodiments without departing from the scope of the invention as described in the specification and defined in the appended claims.

What is claimed is:

1. A system for assaying a fluid sample with excitation radiation from a radiation source, which radiation is capable of exciting fluorescence in fluorescent material, said apparatus comprising:

a totally internally reflecting, unitary elongated fiber transmissive to both the excitation radiation and to the fluorescence, said fiber having an end into which the radiation is to be introduced and a peripheral surface, at least a portion of said peripheral surface being positioned to contact the sample;

a source of the excitation radiation; and optical means for guiding the excitation radiation into said fiber within the bounds of a critical angle to assure total internal reflectance and for focusing the excitation radiation onto said substrate limited substantially to the region thereof at which evanescent wave coupling occurs, said optical means comprising an optical transformer for redirecting a solid collimated beam of light into a beam having an annular cross section of substantially constant cross section and a converging lens between said optical transformer and said fiber for focusing the annular cross section beam from said optical transformer into said fiber.

2. An assay system as set forth in claim 1, wherein said source of the excitation radiation provides a solid collimated beam of light.

3. An assaying system as set forth in claim 2 wherein said optical transformer includes:

a first refractive member having a first leading surface positioned to intercept the circular collimated light beam for transforming the circular collimated light beam into a diverging cone shaped annular light beam and a base surface lying in a plane perpendicular to the axis of the collimated light beam; and a second refractive member having a second leading surface positioned to intercept the diverging annular light beam from said first refractive member for transforming the cone shaped annular light beam into an annular light beam having a substantially constant inner and outer diameters;

said first and second refractive members being spaced apart and coaxial with the longitudinal axis of the circular collimated light beam.

4. An assaying system as set forth in claim 3 wherein said first and second refractive members are transparent.

5. An assaying system as set forth in claim 4 wherein said first refractive member has a leading surface which is a circular cone facing the collimated light beam; and wherein said second refractive member has a leading surface which is a circular cone facing the diverging annular light beam.

6. An assaying system as set forth in claim 1 wherein said elongated fiber is cylindrical, said elongated fiber being positioned to receive a coating of the fluorescent material on at least a portion of said peripheral surface thereof.

7. An assaying system as set forth in claim 1 wherein said elongated fiber is cylindrical, said elongated fiber being positioned to receive on at least a portion of said peripheral surface a coating of the fluorescent material thereof which includes at least a moiety of an antibody-antigen complex that includes a tag that will provide the fluorescence when excited by an evanescent wave generated by the excitation radiation.

8. An assaying system as set forth in claim 1 including:
a hollow elongated enclosure disposed about and spaced from said fiber so as to provide an interspace between said fiber and said enclosure.

9. An assaying system as set forth in claim 8 wherein said fiber is disposed concentrically within said enclosure.

10. An assaying system as set forth in claim 8 wherein the interspace between said enclosure and said fiber is of capillary dimensions.

11. An assaying system as set forth in claim 1 including: detector means for detecting fluorescence radiation emitted from said introduction end of said fiber responsively to the excitation radiation.

12. An assaying system as set forth in claim 1 including:
a hollow elongated enclosure disposed about and spaced from said fiber so as to provide an interspace of capillary dimensions between said fiber and said enclosure, said fiber being disposed coaxially with said enclosure.

13. A optical system for transforming a solid circular collimated light beam to an annular collimated light beam comprising:
a first refractive member having a first leading surface positioned to intercept the circular collimated light beam for transforming the circular collimated light beam into a diverging cone shaped annular light beam and a base surface lying in a plane perpendicular to the axis of the collimated light beam; and a second refractive member having a second leading surface positioned to intercept the diverging annular light beam from said first refractive member for transforming the cone shaped annular light beam into an annular light beam having a substantially constant diameter, said second refractive member having a base lying in a plane transverse to the axis of the collimated light beam;

said first and second refractive members being spaced apart and coaxial with the longitudinal axis of the circular collimated light beam.

14. An optical system as set forth in claim 13 wherein said first and second refractive members are transparent.

15. An optical system as set forth in claim 13 wherein said first refractive member has a leading surface facing the collimated light beam which is a circular cone; and wherein said second refractive member has a leading surface facing the diverging annular light beam which is a circular cone.

16. An optical system for transforming a circular solid collimated light beam into a beam having an annular cross section comprising:
an optical transformer including a sobody having a firbody having a first refractive surface for redirecting a solid collimated light beam into a diverging light beam having an annular cross section and having a second refractive surface for redirecting the diverging light beam into a light beam having an annular cross section of substantially constant diameter.

17. Apparatus as set forth in claim 16 wherein said optical transformer includes:
a first refractive element having a first conical surface onto which the solid collimated light beam is directed for redirecting the light beam into the diverging annular light beam; and a second refractive element having a second conical surface for receiving the diverging annular light beam from said first lens element and for redirecting the diverging annular light beam into a beam having an annular cross section of substantially constant cross section.

18. Apparatus as set forth in claim 16 wherein said optical transformer includes:
a first refractive element positioned to intercept the circular collimated light beam for transforming the circular collimated light beam into a diverging cone shaped annular light beam; and a second refractive element positioned to intercept the diverging annular light beam from said first refractive member for transforming the cone shaped annular light beam into an annular light beam having a substantially constant diameter;

said first and second refractive elements being spaced apart and coaxial with the longitudinal axis of the circular collimated light beam.

19. An optical system as set forth in claim 18 wherein said first refractive element has a leading surface facing the collimated light beam which is a circular cone; and wherein said second refractive element has a leading surface facing the diverging annular light beam which is a circular cone.

* * * * *

UNITED STATES PATENT AND TRADEMARK OFFICE
CERTIFICATE OF CORRECTION

PATENT NO. : 5,639,668

DATED : Jun. 17, 1997

INVENTOR(S) : Neel et al.

It is certified that error appears in the above-identified patent and that said Letters Patent is hereby corrected as shown below:

Column 16, line 24, please delete "sobody having a fir-" and insert --solid transparent--.

Signed and Sealed this

Twenty-first Day of October 1997

Attest:

BRUCE LEHMAN

Attesting Officer

Commissioner of Patents and Trademarks